United States Patent
Curtis

(10) Patent No.: US 7,534,037 B2
(45) Date of Patent: May 19, 2009

(54) METHODS AND APPARATUS FOR ACCELERATING MECHANICAL MEMBERS ASSOCIATED WITH A MOVING SUBSYSTEM ON A MOBILE X-RAY MEDICAL IMAGING SYSTEM

(75) Inventor: Steven Emerson Curtis, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 88 days.

(21) Appl. No.: 11/554,016

(22) Filed: Oct. 28, 2006

(65) Prior Publication Data

US 2008/0101547 A1 May 1, 2008

(51) Int. Cl.
*H05G 1/02* (2006.01)

(52) U.S. Cl. ............ 378/197; 378/198
(58) Field of Classification Search ........ 378/204, 378/11–15, 39, 40, 55, 196–198
See application file for complete search history.

(56) References Cited

U.S. PATENT DOCUMENTS

| | | | |
|---|---|---|---|
| 6,203,196 B1 * | 3/2001 | Meyer et al. ........ 378/197 |
| 6,461,040 B1 * | 10/2002 | Mattson et al. ........ 378/205 |
| 2004/0246554 A1 * | 12/2004 | Kaeriyama ........ 359/223 |
| 2004/0247137 A1 * | 12/2004 | Inoue et al. ........ 381/71.4 |
| 2005/0281391 A1 * | 12/2005 | Luo et al. ........ 378/204 |

OTHER PUBLICATIONS

Charles Jackson, The Practical Vibration Primer, 1979, Gulf Publishing Company, ISBN 0-87201-891-1, pp. 21-30.*
Michael Norton and Denis Karczub, Fundamentals of Noise and Vibration Analysis for Engineers, 2003, Press Syndicate of the University of Cambridge, 2nd Edition, ISBN 0 521 49913 5, pp. 355-365.*
Thomas D. Rossing and Neville H. Fletcher, Principles of Vibration and Sound, Springer-Verlag New York, Inc., 2nd Edition, ISBN 0-387-40556-9, pp. 122-123.*

* cited by examiner

*Primary Examiner*—Edward J Glick
*Assistant Examiner*—Mona M Sanei
(74) *Attorney, Agent, or Firm*—Peter Vogel, Esq.; William Baxter, Esq.; Michael G. Smith, Esq.

(57) ABSTRACT

Methods and apparatus are provided through which mechanical members associated with a moving subsystem on a mobile X-ray medical imaging system are accelerated and decelerated using triangular acceleration and deceleration pulses having pulse widths that do not provide excitation energy that will cause unwanted vibrations in the members.

19 Claims, 8 Drawing Sheets

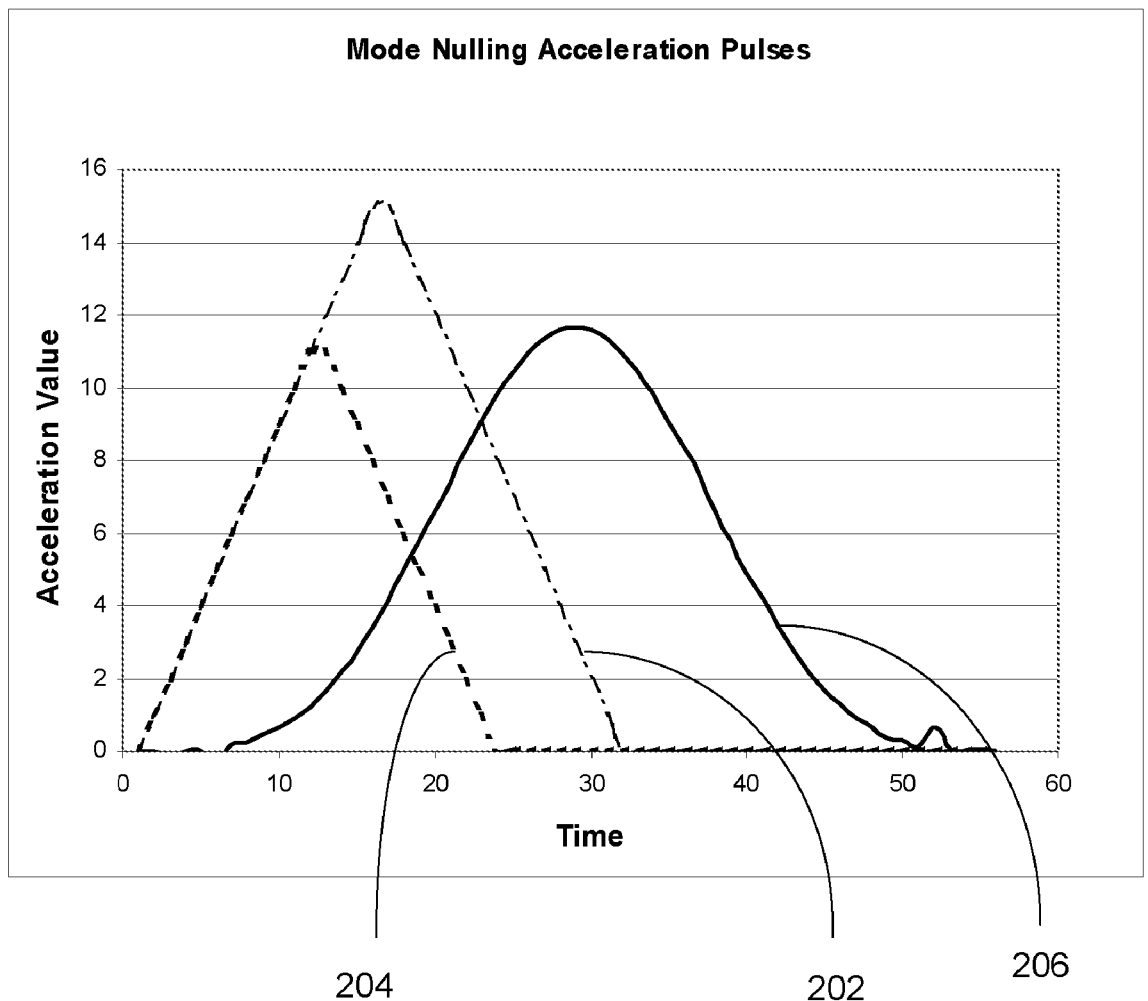
FIG. 2
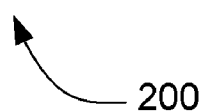

ized. In mobile imaging systems, the C-arm and associated members tend to be lighter in weight and are therefore less robust than fixed systems that can aggravate the mobile system's tendency to vibrate.
METHODS AND APPARATUS FOR ACCELERATING MECHANICAL MEMBERS ASSOCIATED WITH A MOVING SUBSYSTEM ON A MOBILE X-RAY MEDICAL IMAGING SYSTEM

FIELD OF THE INVENTION

This invention relates generally to mobile X-ray medical imaging systems, and more particularly to mobile X-ray medical imaging systems which contain powered motion control for accelerating mechanical members associated with a moving subsystem.

BACKGROUND OF THE INVENTION

Modern medical X-ray imaging systems have become a valuable tool in the healthcare profession. Imaging systems such as basic X-ray, computed tomography (CT) and fluoroscopy systems which were once found only in major medical facilities have become more commonplace due to their affordable cost and compact size. Oftentimes, mobile X-ray imaging systems are utilized outside of radiology rooms because of their ability to be transported to operating rooms or other areas serving multiple purposes, thus providing instant on-the-spot X-ray imaging.

Mobile X-ray medical imaging systems often contain various mechanical members that are typically long and slender in shape. On a typical mobile C-arm X-ray medical imaging system, an X-ray source and image detector are placed in proper proximity to the patient by attaching them to the respective ends of a C-shaped member such that they are located below and above the patient. The C-arm member can then be anchored to other structures on an imaging system through a capturing clamp that can have bearings to allow the C-arm member to slide through the clamp. This one degree of freedom movement allows the user to position the X-ray source and detector more exactly relative to the patient, so as to optimize the desired images. Furthermore, various other motion subsystems can be available on the C-arm that accommodate additional degrees of freedom. For example, the C member can be allowed to twist, or slide horizontally across the patient, or slide in the direction of head to toe of the patient, or move in elevation relative to the patient. Various mechanical members are required to accomplish motions like horizontal and vertical sliding, and these members are also typically long and slender in nature.

More advanced C-arm systems provide powered motion control to assist the user in adjusting some or all of the movements necessary for optimal imaging. This motion control can be accomplished through the use of a joystick, buttons or various foot pedals, for example. During CT/3D imaging, the C-arm traverses a continuous semi-arc around the patient's body as the imaging occurs. During fluoroscopy, the C-arm moves to distinct positions around the patient's body as distinct images are obtained. A computer with imaging software can then construct the desired CT, 3D or 2D images for diagnosis. In order to produce the clearest possible images, it is important that the C-arm not vibrate during the imaging process.

All mechanical members inherently have natural mechanical resonances that will make the member oscillate when it is acted upon by an excitation that contains energy at a mechanical resonance of the member. Likewise, if the member is not acted upon by an excitation that contains energy at a mechanical resonance of the member, the member is less likely to vibrate. Since various members of the C-arm system are long and slender, they can have a tendency to vibrate back and forth when the X-ray source and detector are moving, and can continue to vibrate for a period of time after all intended movements are completed. Such vibrations are due to natural mechanical resonances in these members, the degree of spring, and the mass and moment of inertia of loads attached to the members. In mobile imaging systems, the C-arm and associated members tend to be lighter in weight and are therefore less robust than fixed systems that can aggravate the mobile system's tendency to vibrate.

Depending on various characteristics of the systems, these vibrations can oscillate at frequencies below one cycle per second and up to many tens of cycles per second, and there can be several different vibrations occurring all at once. However, the stronger and more troublesome vibrations tend to be between 0.5 and 5 cycles per second. Because vibration can cause image blur, detailed imaging requires the x-ray source to output very short high powered x-ray pulses to freeze motion, much as a pulsing strobe light freezes motion when viewed optically, (more expensive and typically impractical due to power constraints for mobile equipment), or that the C-arm member not vibrate during image capture because vibration can cause image blur. To reduce the blur associated with the unwanted oscillation, fluoroscopic users of the C-arm may have to wait for these stronger vibrations to die down after completing a powered motion before acquiring an image, or the vibrations can require an assistant to manually stop the system from vibrating. The delay in imaging can also cause additional unnecessary distress to an injured patient who must remain stationary during the imaging process and if numerous images are required, the additional imaging time and the associated distress to the patient caused by the stabilization delay can be significant.

An even more complex mobile X-ray C-arm imaging system is designed to acquire CT or 3D image information by continuously moving the X-ray source and detector about the patient in a controlled way. Such a system can use one or more degrees of freedom from the motion capabilities previously described. In this case, it is important that the motion be smooth so that the location of the X-ray source and detector is known when image data is acquired. Errors in location can result in reconstruction artifacts for the CT or 3D images. However, natural mechanical resonances as those described above, can cause unwanted vibrations to occur while the members are in motion during CT or 3D acquisition.

For the reasons stated above, and for other reasons stated below which will become apparent to those skilled in the art upon reading and understanding the present specification, there is a need in the art for a method to reduce vibrations in the accelerated members of a mobile X-ray imaging system. There is also a need in the art for a mobile X-ray medical imaging system with reduced vibration in the accelerated mechanical members.

BRIEF DESCRIPTION OF THE INVENTION

The above-mentioned shortcomings, disadvantages and problems are addressed herein, which will be understood by reading and studying the following specification.

The invention is directed to a method and apparatus for improved motorized motion of accelerated members of a mobile X-ray medical imaging system.

In one aspect, certain embodiments of the method to reduce vibration in accelerating one or more members of a mobile X-ray imaging apparatus include determining one or more dominant resonant frequencies of one or more mechanical members. The method also includes synthesizing one or more excitation acceleration pulses having substantially no excitation energy at the dominant resonant frequencies of the members and then applying one or more excitation acceleration signals to the members that minimizes excitation energy at the frequencies of the dominant resonant frequencies of the members.

In a further aspect, an embodiment includes determining one or more dominant mechanical resonant frequencies of one or members, synthesizing one or more excitation acceleration pulses having substantially no excitation energy at the dominant resonant frequencies of the member and then applying one or more excitation acceleration signals to the member that minimizes excitation energy at the frequencies of the dominant mechanical resonant frequencies to accelerate the member to a cruising velocity. The method also includes synthesizing one or more excitation deceleration pulses having substantially no excitation energy at the dominant resonant frequencies of the member and then applying one or more excitation deceleration signals to the member that minimizes excitation energy at the frequencies of the dominant mechanical resonant frequencies.

In yet a further aspect, a mobile X-ray medical imaging apparatus with reduced vibration motion control includes a mobile X-ray medical imaging system with at least one moveable C-arm member and a motion controller for accelerating the C-arm member wherein the controller outputs at least one triangle acceleration pulse having a pulse width that substantially reduces unwanted vibrations in the member.

In still yet a further aspect, a mobile X-ray medical imaging apparatus with reduced vibration motion control includes a mobile X-ray medical imaging system with at least one moveable C-arm member and a motion controller for decelerating the C-arm member wherein the controller outputs at least one negative triangle deceleration pulse for decelerating the member that substantially reduces unwanted vibrations in the member.

Apparatus, systems, and methods of varying scope are described herein. In addition to the aspects and advantages described in this summary, further aspects and advantages will become apparent by reference to the drawings and by reading the detailed description that follows.

BRIEF DESCRIPTION OF THE DRAWINGS

FIG. 2 is a plot of two triangular acceleration pulses and the resulting convolution in accordance with an embodiment.

DETAILED DESCRIPTION OF THE INVENTION

In the following detailed description, reference is made to the accompanying drawings that form a part hereof, and in which is shown by way of illustration specific embodiments that can be practiced. These embodiments are described in sufficient detail to enable those skilled in the art to practice the embodiments, and it is to be understood that other embodiments can be utilized and that logical, mechanical, electrical and other changes can be made without departing from the scope of the embodiments. The following detailed description is, therefore, not to be taken in a limiting sense.

Method Embodiments

Figure 1:
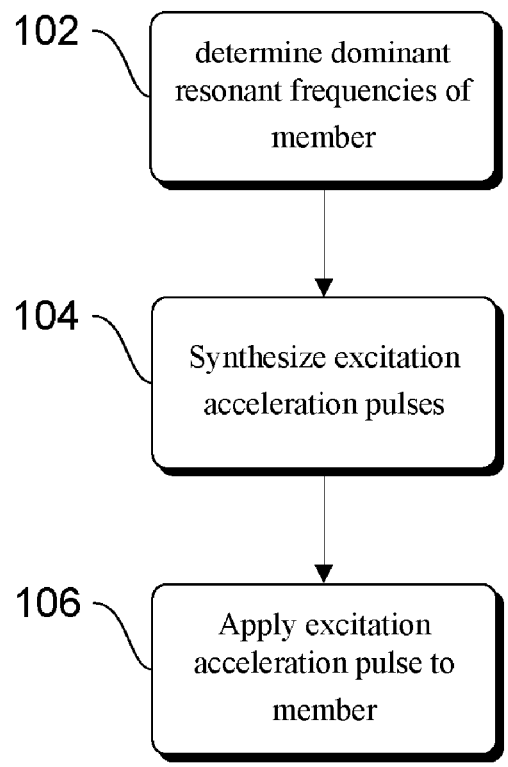
FIG. 1 illustrates a method for accelerating mechanical members associated with a moving subsystem on a mobile X-ray medical imaging system without providing excitation energy that will cause unwanted vibrations in accordance with an embodiment.
Figure 1:
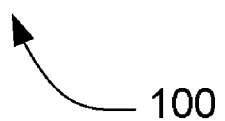

FIG. 1 illustrates a method 100 for accelerating mechanical members associated with a moving subsystem on a mobile X-ray medical imaging system without providing excitation energy that will cause unwanted vibrations in accordance with an embodiment. In action 102, the resonant frequencies of the member desired to be accelerated are determined. According to an embodiment, the resonant frequencies can be determined by performing a detailed finite element analysis on the member, by performing a vibration survey on the member, or by exciting the member with an impulse function and counting the oscillations per period of time to determine the dominant resonant frequency. Any other common method of determining the resonant frequencies of mechanical members can also be used.

In action 104, one or more excitation acceleration pulses having little or no excitation energy at the dominant resonant frequency or frequencies of the member are synthesized by the mobile X-ray medical imaging system's motion controller. In one embodiment, the excitation acceleration pulse is a single triangle acceleration pulse having a pulse width that provides little or no excitation energy at the most dominant resonant frequency of the member. In another embodiment, the acceleration pulse is a convolved triangle acceleration pulse comprising more than one triangle pulse wherein each pulse has a pulse width that provides substantially no excitation at two or more resonant frequencies of the member.

The spectrum of the energy produced by an excitation that causes physical motion can be represented by the Fourier transform of the plot of that excitation acceleration plotted against time. The Fourier transform of a triangle acceleration pulse has a since shape which contains various energy nulls in the frequency spectrum. These energy nulls are inversely proportional to the width of the triangle pulse (e.g., the length of time for the triangular acceleration to occur). Once the dominant resonant frequencies of the member are known, one or more specialized triangular acceleration pulses can be configured to provide little or no energy at the dominant resonant frequency or frequencies of the mechanical member while also providing the desired cruising velocity by adjusting the pulse width and magnitude of the triangular acceleration pulses to place energy nulls at the dominant resonant frequencies of the member or at any other desired frequency and by adjusting the pulse magnitude so that the pulse area provides the required cruising velocity. The Fourier transform of that triangular acceleration pulse (or of the convolved pulse if more than one pulse is used) enables the designer to determine the appropriate pulse width to create energy nulls at the more troublesome resonance frequencies that can cause the member to vibrate and ultimately affect image clarity.

For instance, FIG. 2 is a plot of two triangular acceleration pulses and the resulting convolution in accordance with an embodiment. Curve 202 is a first triangular acceleration pulse, curve 204 is a second triangular acceleration pulse and curve 206 is the resulting convolution of the two separate pulses. Curve 202 need not be a similar triangle shape relative to curve 204 and can have a different acceleration value (i.e., magnitude) and pulse width.

Figure 3:
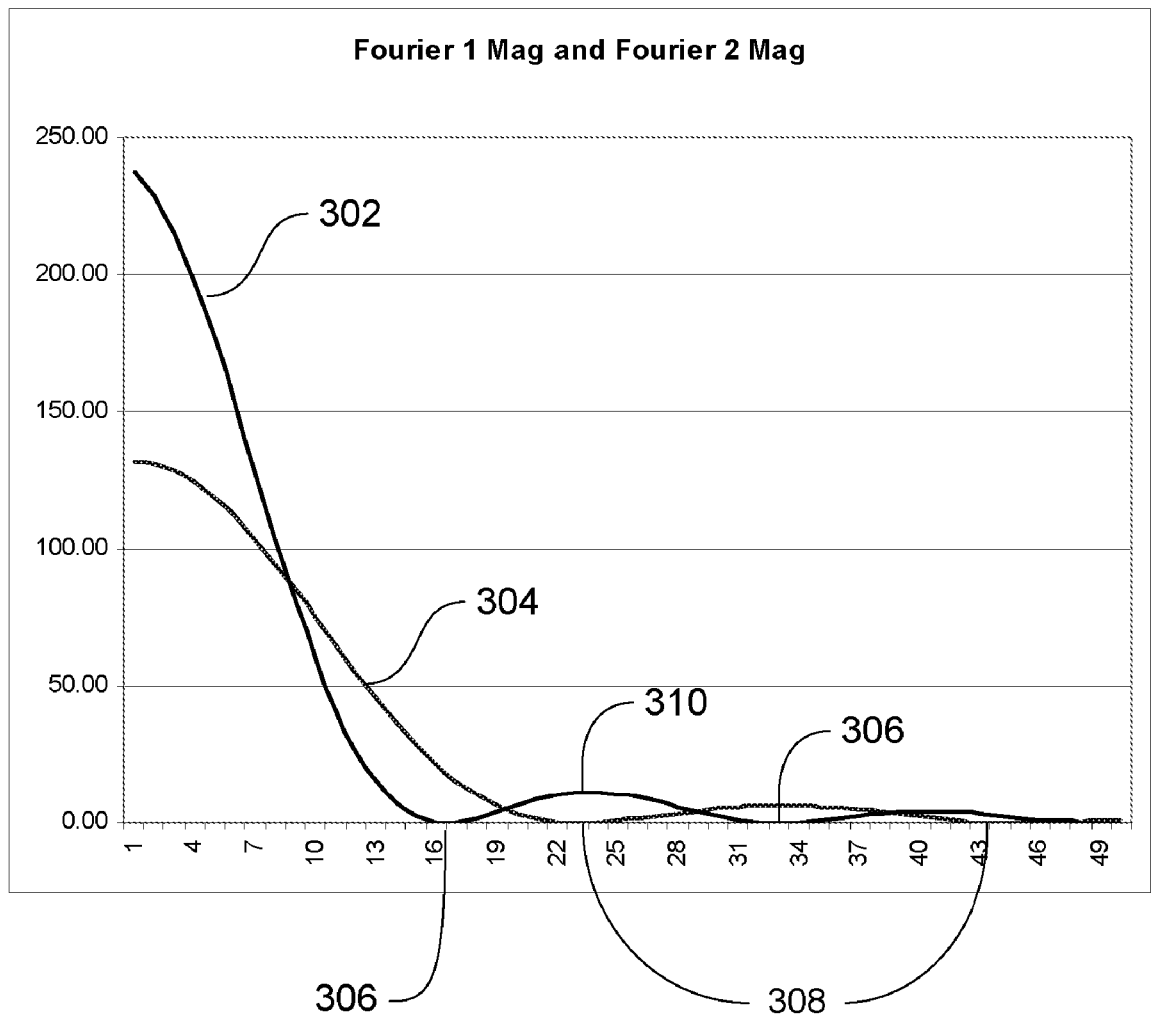
FIG. 3 is a plot of the Fourier transform of the triangular acceleration pulses illustrated in FIG. 2.

FIG. 3 is a plot of the Fourier transforms of two triangular acceleration pulses 202 and 204 shown in FIG. 2. Both curves 302 and 304 have $sinc^2$ shapes and display the spectral locations of the energy nulls 306, 308 for each of the separate triangular acceleration pulses 202 and 204. Curve 302 represents the Fourier transform of curve 202 and curve 304 represents the Fourier transform of curve 204. The pulse width of curve 202 has been chosen to produce energy nulls 306 on curve 302 to correspond to the dominant resonant frequency of a particular C-arm member. By choosing the appropriate a first triangle acceleration pulse 202 having a pulse width that produce energy nulls 306 at the member's dominant resonant frequency, the tendency of the C-arm to vibrate at the member's dominant resonant frequency is significantly reduced.

To further reduce vibrations a second triangle acceleration pulse can be synthesized having a pulse width chosen to produce the energy nulls 308 on curve 304, the first null of which corresponds to the first secondary energy peak 310 on curve 302. The energy nulls 308 will reduce the energy peaks 310 produced by the first triangle acceleration pulse 202 to reduce the energy provided to the system above some specified frequency resulting in a significant reduction in the tendency of the member to vibrate.

Figure 4:
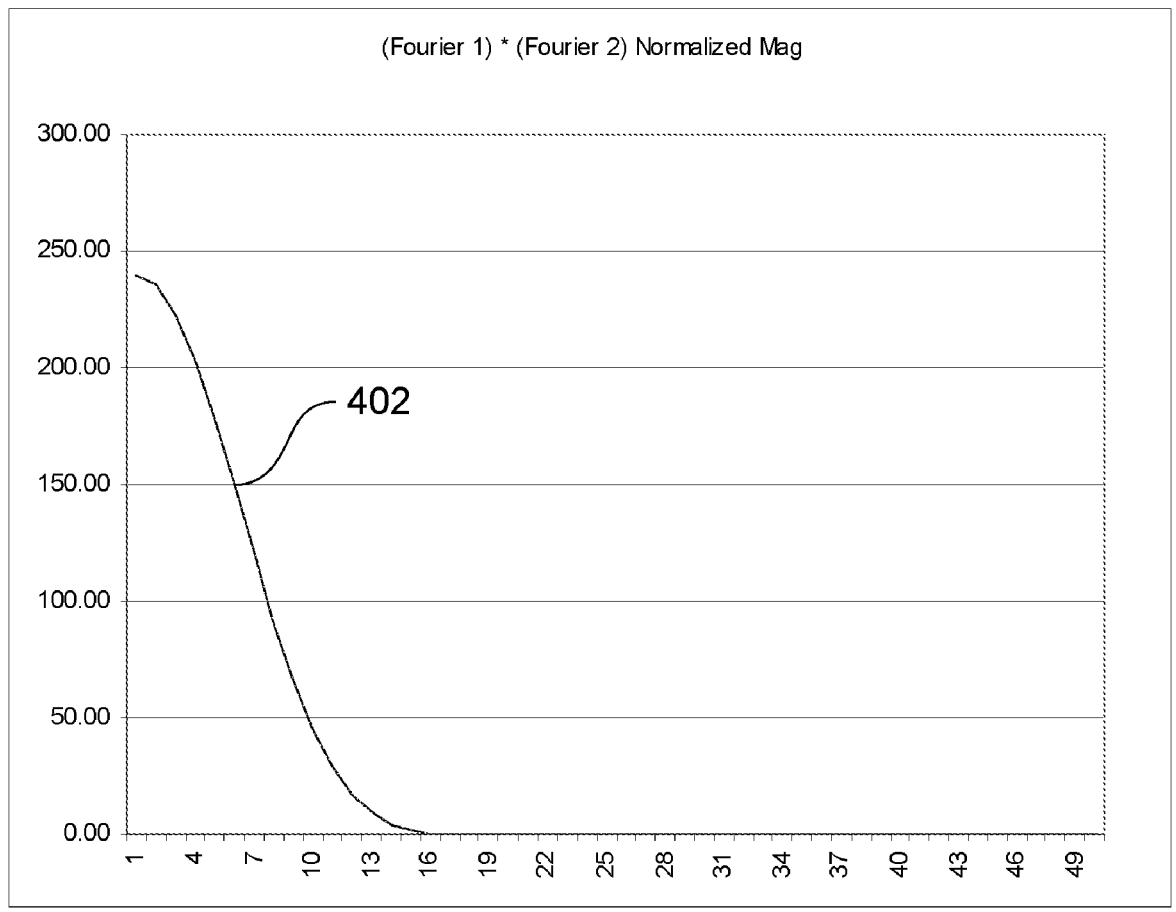
FIG. 4 is a plot of the Fourier transform of the convolution of two triangle acceleration pulses in accordance with an embodiment.

FIG. 4 is a plot of the Fourier transform of the convoluted pulse 206 of triangular acceleration pulses 202 and 204 in accordance with an embodiment. Curve 402 represents a scaled Fourier transform of the first triangular acceleration pulse of curve 202 times the Fourier transform of a second triangular acceleration pulse of curve 204. By choosing the appropriate pulse widths of the triangular acceleration pulses 202, 204, the energy null 308 can be manipulated to negate the first secondary energy peak 310 of the first triangle pulse 302 resulting in greater attenuation of excitation energy over a broader spectrum of frequencies than is obtained by either individual triangular acceleration pulse 202 or 204. Thus, when properly synthesized, pulse 206 will provide even less excitation to one or more resonant frequencies of the mechanical members that the user wishes to accelerate.

In action 106, the specialized acceleration pulse 202 or the convolution of two or more pulses 206 are applied to the member by the mobile X-ray imaging system's motion controller to accelerate the particular mechanical member to its desired cruising velocity with little or no spectral energy at the member's dominant resonant frequency which substantially reduces the tendency for the member to vibrate.

Furthermore, the final cruising velocity of a mobile X-ray medical imaging system's C-arm member or similar mechanism accelerated with a triangle pulse can be manipulated by adjusting the height and width of the triangle pulses as the final cruising velocity of the accelerated member is dependent on both the height and the width of the triangle or the area under the pulse while the regions of spectral attenuation are determined only by the width. Thus, after determining the dominant resonant frequencies of the mechanical member to be accelerated, the motion excitement applied to the mobile C-arm member can be shaped such that no spectral energy is applied to the C-arm member at the dominant resonant frequency of the member while also achieving the desired cruising velocity of the mechanism in motion. If a convolved triangle acceleration pulse 206 is used, the convolved triangular pulse 206 requires a length of time equal to the sum of the time lengths of the individual triangle pulse building blocks 202, 204.

In another embodiment, the excitation acceleration pulse applied to the member is a convolution of two triangle acceleration pulses wherein the first triangle acceleration pulse has a pulse width that provides a spectral energy null at a first desired mechanical resonant frequency of the member but has a secondary energy peak at a second frequency and the second triangle pulse has a pulse width that has a spectral energy null at the frequency of the first secondary energy peak of the first triangle acceleration pulse. Additional triangle acceleration pulses can be combined to nullify additional energy peaks if a further reduction in vibration is desired.

In another embodiment, the excitation acceleration pulse applied to the member is a convolution of two triangle acceleration pulses wherein the first triangle acceleration pulse has a pulse width that provides a spectral energy null at a first frequency which can be a frequency other than the resonant frequency of the accelerated member. This first triangle acceleration pulse will necessarily have a first secondary energy peak at a second frequency which can be attenuated by a second triangular acceleration pulse having the appropriate pulse width. Specifically, if the pulse width of the second triangle acceleration pulse is chosen such that it provides a spectral energy null at the second frequency of the first secondary energy peak of the first triangle acceleration pulse, the energy will be attenuated above that first frequency. The overall effect of using these specially configured acceleration pulses is a reduction of vibration in the accelerated member above a desired frequency dependent upon the pulse widths chosen by the designer. Additional triangle acceleration pulses can be combined to nullify additional energy peaks if a further reduction in vibration is desired.

Figure 5:
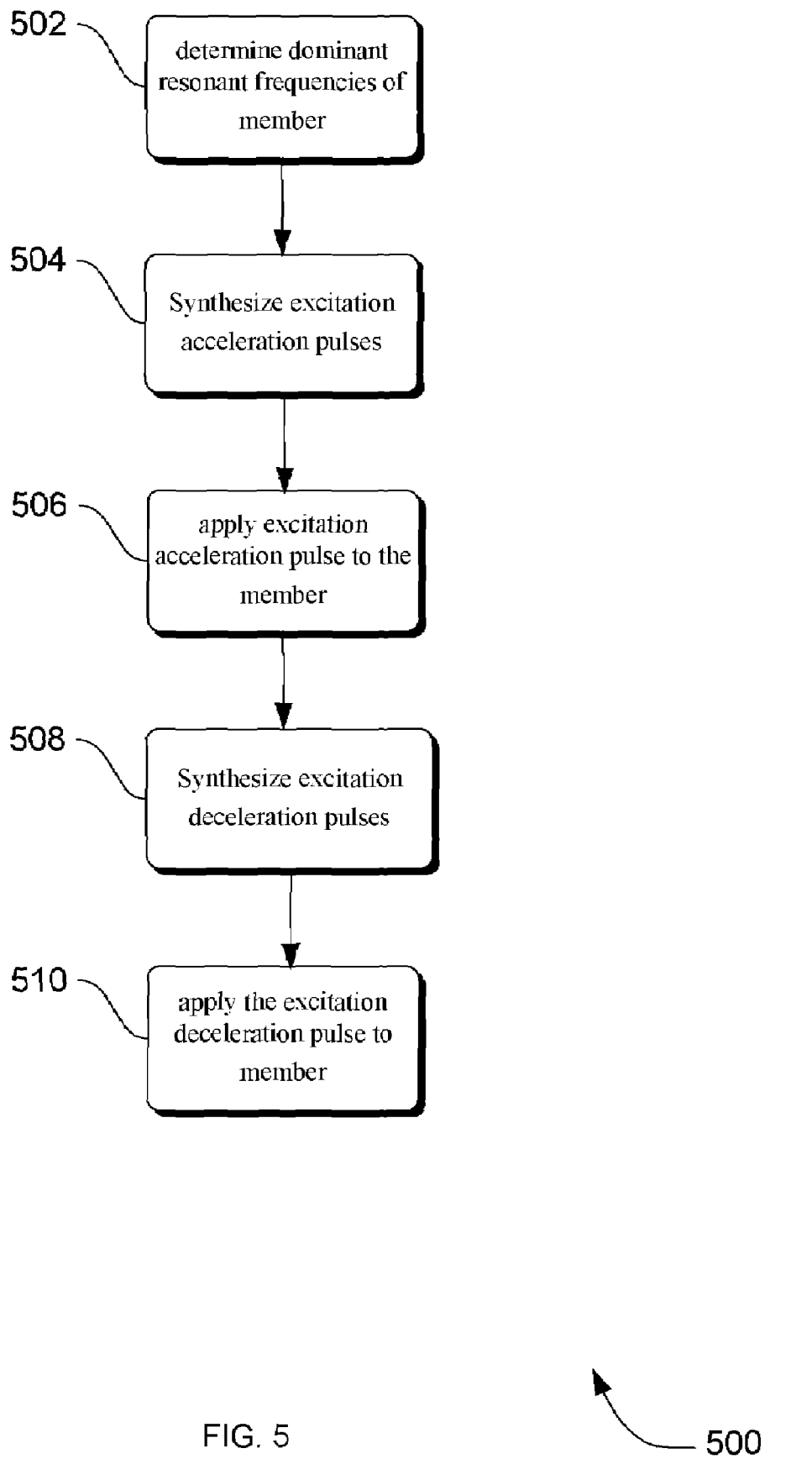
FIG. 5 illustrates a method for accelerating mechanical members associated with a moving subsystem on a mobile X-ray medical imaging system to a cruising velocity and then decelerating that member back to zero velocity without providing excitation energy that will cause unwanted vibrations in accordance with an embodiment.

FIG. 5 illustrates a method 500 for accelerating mechanical members associated with a moving subsystem on a mobile X-ray medical imaging system to a cruising velocity and then decelerating that member back to zero velocity without providing excitation energy that will cause unwanted vibrations in accordance with an embodiment.

At action 502, the resonant frequencies of the member desired to be accelerated are determined. According to an embodiment, the resonant frequencies can be determined by performing a detailed finite element analysis on the member, or by performing a vibration survey on the member, or by exciting the member with an impulse function and counting the oscillations per period of time to determine the dominant resonant frequency.

In action 504, one or more excitation acceleration pulses having little or no excitation energy at the dominant resonant frequency or frequencies of the member are synthesized by the mobile X-ray medical imaging system's motion controller.

In action 506, the specialized acceleration pulse or the convolution of two or more pulses are applied to the member by the mobile X-ray imaging systems motion controller to accelerate the particular mechanical member to its desired cruising velocity with little or no spectral energy at the member's dominant resonant frequency which significantly reduces the tendency for the member to vibrate.

In action 508, one or more excitation deceleration pulses having little or no excitation energy at the dominant resonant frequency or frequencies of the member are synthesized by the mobile X-ray medical imaging system's motion controller.

In action 510, the specialized deceleration pulse or the convolution of two or more pulses are applied to the member by the mobile X-ray imaging systems motion controller to decelerate the member to zero velocity with little or no spectral energy at the member's dominant resonant frequency which substantially reduces the tendency for the member to vibrate during deceleration.

In one embodiment, the excitation acceleration pulse is a single triangle acceleration pulse having a pulse width that provides little or no excitation energy at the most dominant resonant frequency of the member. In another embodiment, the acceleration pulse is a convolved triangle acceleration pulse comprising more than one triangle pulse wherein each pulse has a pulse width that provides substantially no excitation at two or more resonant frequencies of the member.

In another embodiment, the excitation acceleration pulse applied to the member is a convolution of two triangle acceleration pulses wherein the first triangle acceleration pulse has a pulse width that provides a spectral energy null at a first desired mechanical resonant frequency of the member but has a secondary energy peak at a second frequency and the second triangle pulse has a pulse width that has a spectral energy null at the frequency of the first secondary energy peak of the first triangle acceleration pulse and to generally reduce all spectral energy beyond the first nulling region of the first triangular pulse. Additional triangle acceleration pulses can be combined to nullify additional energy peaks if a further reduction in vibration is desired.

In another embodiment, the member previously accelerated is decelerated back to zero velocity by the use of a single negative triangle deceleration pulse having a pulse width that creates little or no spectral energy at the dominant resonant frequency of the member.

In another embodiment, a convolved deceleration pulse comprising more than one triangle deceleration pulse can be applied to the member wherein each pulse comprises different pulse widths to provide spectral energy nulls at different resonant frequencies of the member.

In yet another embodiment, a convolved deceleration pulse comprising more than one triangle deceleration pulse can be applied to the member wherein the convolved pulse comprises a first triangle deceleration pulse containing no spectral energy at the dominant resonant frequency but having secondary energy peaks at higher frequencies and one or more additional triangle pulses containing a spectral energy null at the first secondary energy peak of the first triangle deceleration pulse and to generally reduce all spectral energy beyond the first nulling region of the first triangular pulse.

In yet another embodiment, the excitation deceleration pulse applied to the member is a convolution of two triangle deceleration pulses wherein the first triangle deceleration pulse has a pulse width that provides a spectral energy null at a first frequency which can be a frequency other than the resonant frequency of the accelerated member. This first triangle deceleration pulse will necessarily have a first secondary energy peak at a second frequency which can be attenuated by a second triangular deceleration pulse having the appropriate pulse width. Here, the pulse width of the second triangle deceleration pulse is chosen such that it provides a spectral energy null at the second frequency of the first secondary energy peak of the first triangle deceleration pulse to attenuated the energy supplied to the member above that first frequency. Additional triangle deceleration pulses can be combined to nullify additional energy peaks if a further reduction in vibration is desired. Thus members can be decelerated back to zero for imaging such as fluoroscopy with a reduction in system vibration.

Apparatus Embodiments

Figure 6:
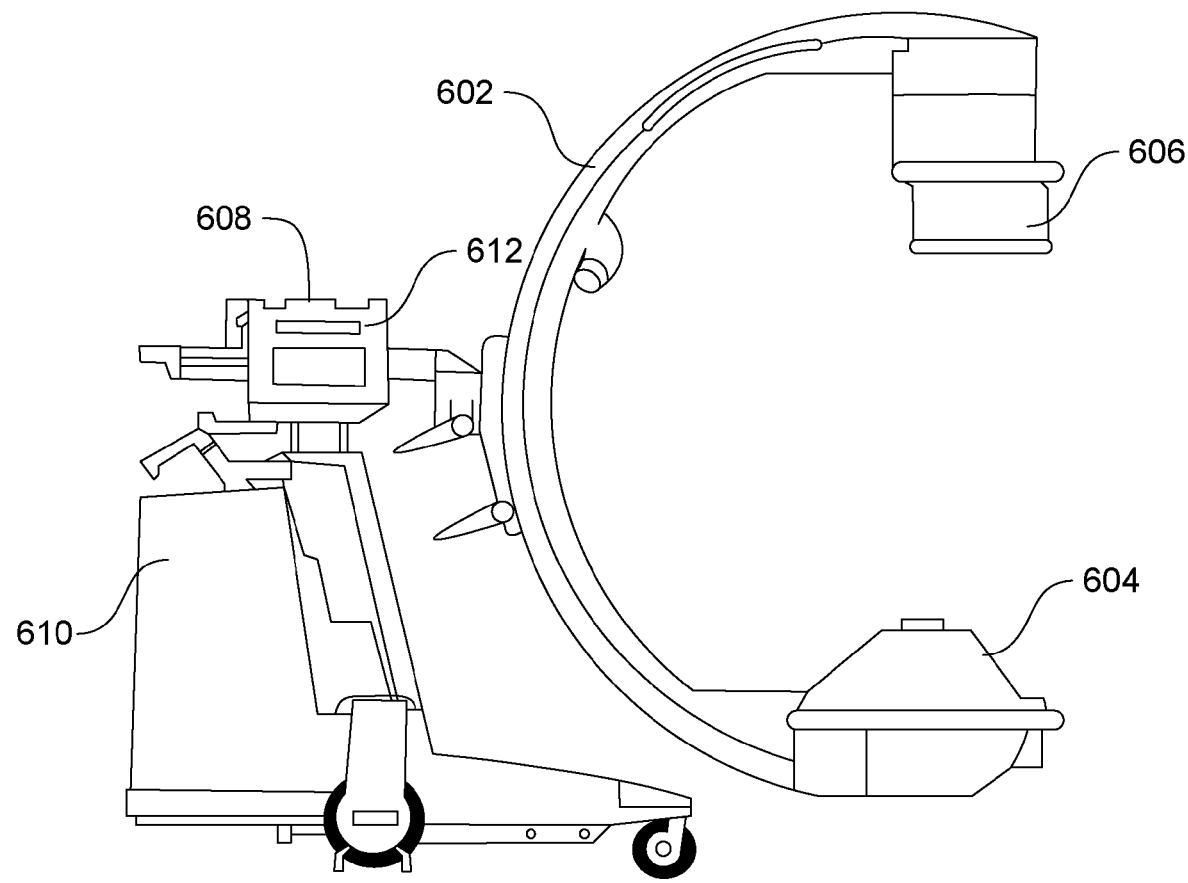
FIG. 6 is an illustration of a mobile X-ray medical imaging system used in accordance with an embodiment.

FIG. 6 is an illustration of a mobile X-ray medical imaging apparatus used in accordance with an embodiment. System 600 generally includes a C-arm 602 having an X-ray source 604 at one end of the C-arm 602 and an image receptor 606 at the opposite end of the C-arm 602. The C-arm 602 is pivotably mounted to a support structure 608 that contains a motion controller 612 that provides powered motion to move the C-arm into position for imaging. The support structure 608 is mounted on a wheeled base 610 that allows the system 600 to be moved from place to place.

Figure 7:
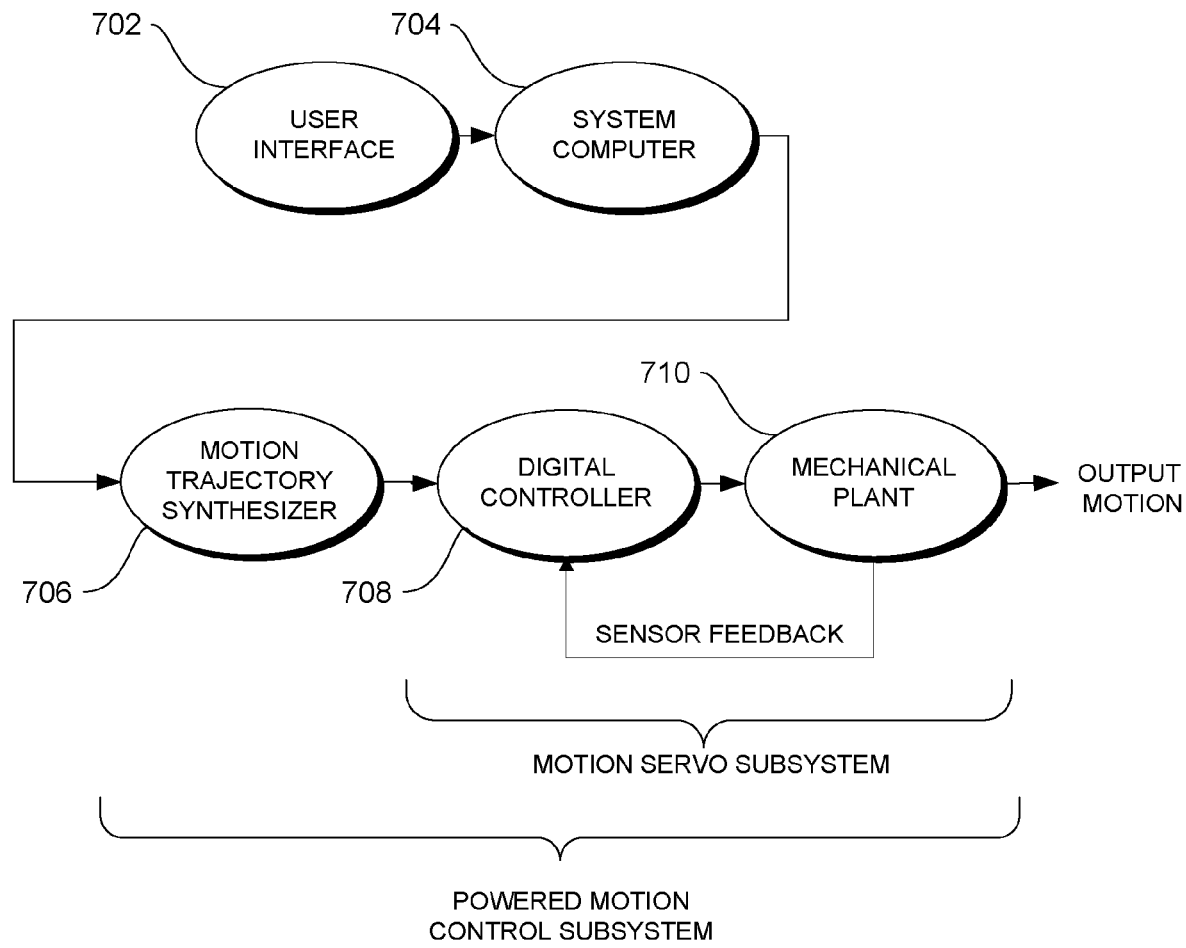
FIG. 7 illustrates a powered motion controller in accordance with an embodiment.

FIG. 7 illustrates a powered motion controller apparatus in accordance with an embodiment. The motion controller 700 includes a user interface 702, a system computer 704, a motion trajectory synthesizer 706, a digital controller 708 and a mechanical plant 710. The user interface 702 provides manual position controls to move the C-arm into specific desired positions, CT/3d initiation controls to initiate or terminate imaging scans and various other controls for other C-arm subsystems. These controls can be operable by one or more joystick or foot pedals or from a computer screen with a graphical interface. The user interface sends the desired system commands to the system computer 704 that provides output commands to the various C-arm subsystem interfaces as well as to the powered motion control subsystem.

The powered motion control subsystem includes the motion trajectory synthesizer 706 and the motion servo subsystem that includes the digital controller 708 and the mechanical plant 710 containing the motor power sources, one or more C-arm motors and various position sensors.

The output of the motion trajectory synthesizer provides the acceleration pulses to move the C-arm members 602 to their desired position by using one or more specialized triangular acceleration pulses having pulse widths that contain no energy at the mechanical resonances of the C-arm members. The output of the motion trajectory synthesizer also provides the negative triangle deceleration pulses to decelerate the C-arm member from a cruising velocity to zero velocity. If a negative triangle deceleration pulse is chosen such that the pulse width provides no spectral energy at the dominant resonant frequencies of the C-arm members 602, the C-arm member 602 will have a reduced tendency to vibrate as the member is accelerated and decelerated.

The technical effect of system 700 is the reduction of vibration in C-arm members 602 of a mobile X-ray imaging system 600 during image acquisition for either fluoroscopy or CT/3d imaging by using motion excitement that avoids spectral energy at the mechanical resonances of the C-arm members 602. Since the C-arm member is less likely to vibrate during powered motion, image scans can be performed faster or with more accuracy than in previous systems. It also allows for the physical design structure of a various C-arm member of a mobile C-arm medical imaging system to be lighter in weight than those normally required in traditional systems.

Hardware and Operating Environment

Figure 8:
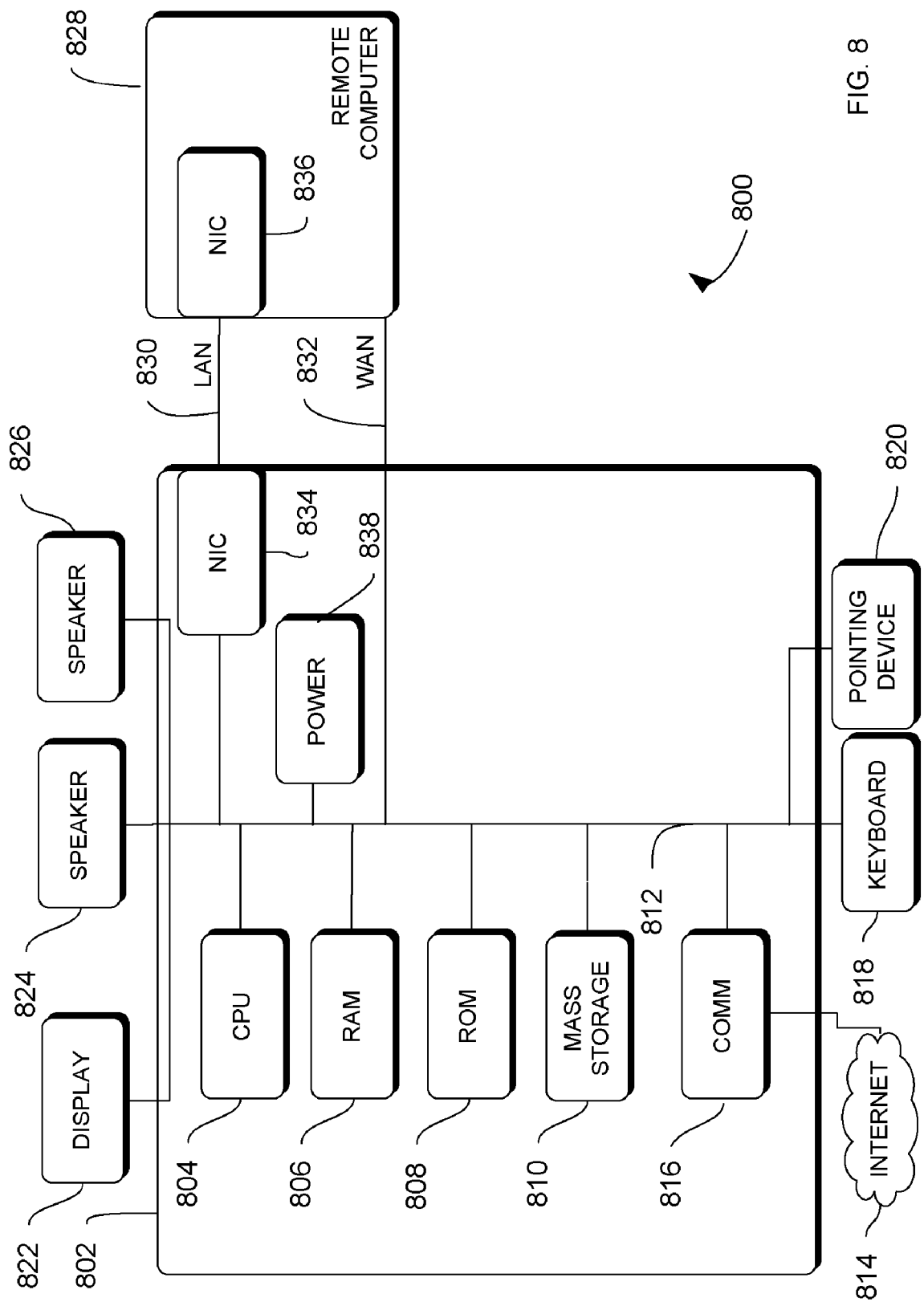
FIG. 8 is a block diagram of the hardware and operating environment in which different embodiments can be practiced.

FIG. 8 is a block diagram of the hardware and operating environment 800 in which different embodiments can be practiced. The description of FIG. 8 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 802 includes a processor 804, commercially available from Intel, Motorola, Cyrix and others. Computer 802 also includes random-access memory (RAM) 806, read-only memory (ROM) 808, and one or more mass storage devices 810, and a system bus 812, that operatively couples various system components to the processing unit 804. The system bus 812, as defined here, can include various means of communication, including parallel and/or serial data bit transportation mediums, various forms of video information routing, various forms of audio information routing, and the like. The memory 806, 808, and mass storage devices, 810, are types of computer-accessible media. Mass storage devices 810 are more specifically types of nonvolatile computer-accessible media and can include one or more hard disk drives, floppy disk drives, optical disk drives, and tape cartridge drives. The processor 804 executes computer programs stored on the computer-accessible media.

Computer 802 can be communicatively connected to the Internet 814 via a communication device 816. Internet 814 connectivity is well known within the art. In one embodiment, a communication device 816 is a modem that responds to communication drivers to connect to the Internet via what is known in the art as a "dial-up connection." In another embodiment, a communication device 816 is an Ethernet® or similar hardware network card connected to a local-area network (LAN) that itself is connected to the Internet via what is known in the art as a "direct connection" (e.g., T1 line, etc.).

A user enters commands and information into the computer 802 through input devices such as a keyboard 818 or a pointing device 820. The keyboard 818 permits entry of textual information into computer 802, as known within the art, and embodiments are not limited to any particular type of keyboard. Pointing device 820 permits the control of the screen pointer provided by a graphical user interface (GUI) of operating systems such as versions of Microsoft Windows®. Embodiments are not limited to any particular pointing device 820. Such pointing devices include mice, touch pads, trackballs, remote controls and point sticks. Other input devices (not shown) can include a microphone, joystick, game pad, satellite dish, scanner, or the like.

In some embodiments, computer 802 is operatively coupled to a display device 822. Display device 822 is connected to the system bus 812. Display device 822 permits the display of information, including computer, video and other information, for viewing by a user of the computer. Embodiments are not limited to any particular display device 822. Such display devices include cathode ray tube (CRT) displays (monitors), as well as flat panel displays such as liquid crystal displays (LCD's). In addition to a monitor, computers typically include other peripheral input/output devices such as printers (not shown). Speakers 824 and 826 provide audio output of signals. Speakers 824 and 826 are also connected to the system bus 812.

Computer 802 also includes an operating system (not shown) that is stored on the computer-accessible media RAM 806, ROM 808, and mass storage device 810, and is executed by the processor 804. Examples of operating systems include Microsoft Windows®, Apple MacOS®, Linux®, UNIX®. Examples are not limited to any particular operating system, however, and the construction and use of such operating systems are well known within the art.

Embodiments of computer 802 are not limited to any type of computer 802. In varying embodiments, computer 802 comprises a PC-compatible computer, a MacOS®-compatible computer, a Linux®-compatible computer, or a UNIX®-compatible computer. The construction and operation of such computers are well known within the art.

Computer 802 can be operated using at least one operating system to provide a graphical user interface (GUI) including a user-controllable pointer. Computer 802 can have at least one web browser application program executing within at least one operating system, to permit users of computer 802 to access intranet or Internet world-wide-web pages as addressed by Universal Resource Locator (URL) addresses. Examples of browser application programs include Netscape Navigator® and Microsoft Internet Explorer®.

The computer 802 can operate in a networked environment using logical connections to one or more remote computers, such as remote computer 828. These logical connections are achieved by a communication device coupled to, or a part of, the computer 802. Embodiments are not limited to a particular type of communications device. The remote computer 828 can be another computer, a server, a router, a network PC, a client, a peer device or other common network node. The logical connections depicted in FIG. 8 include a local-area network (LAN) 830 and a wide-area network (WAN) 832. Such networking environments are commonplace in offices, enterprise-wide computer networks, intranets and the Internet.

When used in a LAN-networking environment, the computer 802 and remote computer 828 are connected to the local network 830 through network interfaces or adapters 834, which is one type of communications device 816. Remote computer 828 also includes a network device 836. When used in a conventional WAN-networking environment, the computer 802 and remote computer 828 communicate with a WAN 832 through modems (not shown). The modem, which can be internal or external, is connected to the system bus 812. In a networked environment, program modules depicted relative to the computer 802, or portions thereof, can be stored in the remote computer 828.

Computer 802 also includes power supply 838. Each power supply can be a battery.

CONCLUSION

Methods and systems for accelerating mechanical members associated with a moving subsystem on a mobile X-ray medical imaging system without providing excitation energy that will cause unwanted vibrations are described. Although specific embodiments are illustrated and described herein, it will be appreciated by those of ordinary skill in the art that any arrangement which is calculated to achieve the same purpose can be substituted for the specific embodiments shown. This application is intended to cover any adaptations or variations.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that the embodiments for accelerating and decelerating mobile C-arm members described herein can be practiced separately or in any combination as may be practical. One of skill in the art will readily recognize that embodiments are applicable to current and future mobile C-arm devices utilizing motion controllers where a reduction in vibration of accelerating and decelerating members is desired.

The terminology used in this application with respect to mobile X-ray medical imaging systems and the motion controllers used therein is meant to include all mobile or portable imaging systems, X-ray system environments and alternate technologies which provide the same functionality as described herein

I claim:

1. A method comprising:
   determining at least one dominant resonant frequency of a mechanical member;
   synthesizing at least one excitation acceleration pulse having substantially no excitation energy at the at least one dominant resonant frequency of the member; and
   applying the at least one excitation acceleration pulse to the member to accelerate the member to a cruising velocity while minimizing excitation energy at the at least one dominant resonant frequency of the member,
   wherein the at least one excitation acceleration pulse further comprises a convolved pulse comprising:
      a first acceleration pulse having a first pulse width having substantially no excitation energy at a first frequency and a first secondary energy peak at a second frequency of the accelerated member; and
      a second acceleration pulse having a second pulse width having substantially no excitation energy at the first secondary energy peak at the second frequency of the first acceleration pulse.

2. The method of claim 1 wherein determining the at least one dominant resonant frequency of the mechanical member further comprises:
   exciting the mechanical member with an impulse function to cause oscillations in the member; and
   counting the oscillations of the mechanical member over a period of time.

3. The method of claim 1 wherein determining the at least one dominant resonant frequency of the mechanical member further comprises:
   performing a finite element analysis on the member.

4. The method of claim 1 wherein the first acceleration pulse further comprises a first triangular acceleration pulse and wherein the second acceleration pulse further comprises a second triangular acceleration pulse.

5. The method of claim 4 wherein the applying further comprises choosing the second pulse width to negate the first secondary energy peak of the first acceleration pulse.

6. The method of claim 1 wherein the member further comprises a moveable C-arm member of a mobile X-ray medical imaging system.

7. The method of claim 1 wherein the first frequency of the accelerated member further comprises a dominant resonant natural frequency of the accelerated member.

8. A method comprising:
   determining a dominant resonant frequency of at least one mechanical member;
   synthesizing at least one excitation acceleration pulse having substantially no excitation at the dominant resonant frequency of the at least one mechanical member;
   applying the at least one excitation acceleration pulse to the at least one mechanical member that minimizes excitation energy at the dominant resonant frequency to accelerate the at least one mechanical member to a cruising velocity;
   synthesizing at least one excitation deceleration pulse having substantially no excitation at the dominant resonant frequency of the at least one mechanical member; and
   applying the at least one excitation deceleration pulse to the at least one mechanical member that minimizes excitation energy at the dominant mechanical resonant frequency,
   wherein the excitation acceleration pulse further comprises:
      a first acceleration pulse having a first pulse width having substantially no excitation energy at a first frequency and a first secondary energy peak at a second frequency; and
      a second acceleration pulse having a second pulse width having substantially no excitation energy at the first secondary energy peak at the second frequency of the first acceleration pulse.

9. The method of claim 8 wherein the excitation acceleration pulse further comprises a convolution of the two acceleration pulses.

10. The method of claim 8 wherein the at least one excitation deceleration pulse further comprises a convolution of two deceleration pulses.

11. The method of claim 8 wherein the applying further comprises choosing the second pulse width to negate the first secondary energy peak of the first acceleration pulse.

12. The method of claim 8 wherein the at least one mechanical member further comprises a moveable C-arm member of a mobile X-ray medical imaging system.

13. The method of claim 8 wherein the first acceleration pulse further comprises a first triangular acceleration pulse and wherein the second acceleration pulse further comprises a second triangular acceleration pulse.

14. The method of claim 8 wherein the first frequency further comprises the dominant resonant frequency of the at least one mechanical member.

15. A mobile X-ray medical imaging apparatus comprising
   a mobile X-ray medical imaging system with at least one moveable C-arm member;
   a motion controller for accelerating the C-arm member wherein the controller outputs energy nulls; and
   a motion trajectory synthesizer that is operable to output a convolved pulse comprising:
      a first triangular acceleration pulse having a first pulse width having the energy nulls at a first dominant frequency and a first secondary energy peak at a second dominant frequency of the member; and
      a second triangular acceleration pulse having a second pulse width having the energy nulls at the first secondary energy peak at the second dominant frequency of the member.

16. The apparatus of claim 15 wherein the motion controller further comprises:
   a motion controller for decelerating the C-arm member wherein the controller outputs at least one triangle deceleration pulse having a pulse width that substantially reduces unwanted vibrations in the member.

17. The apparatus of claim 15 wherein the motion controller further accelerates the member to a cruising velocity and then decelerates the member back to zero velocity.

18. The apparatus of claim 15 wherein the motion controller further accelerates the member to a cruising velocity with de minimis spectral energy at a dominant resonant frequency.

19. The apparatus of claim 15 wherein the motion controller further accelerates the member to a cruising velocity with de minimis spectral energy at a dominant resonant frequency and then decelerates the member back to zero velocity.

* * * * *